US010363035B2

(12) United States Patent
Harris et al.

(10) Patent No.: US 10,363,035 B2
(45) Date of Patent: Jul. 30, 2019

(54) STAPLER TOOL WITH ROTARY DRIVE LOCKOUT

(71) Applicant: Ethicon Endo-Surgery, LLC, Guaynabo, PR (US)

(72) Inventors: Jason L. Harris, Lebanon, OH (US); Michael J. Vendely, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 386 days.

(21) Appl. No.: 15/238,389

(22) Filed: Aug. 16, 2016

(65) Prior Publication Data
US 2018/0049741 A1 Feb. 22, 2018

(51) Int. Cl.
*A61B 17/072* (2006.01)
*A61B 34/30* (2016.01)

(52) U.S. Cl.
CPC ...... *A61B 17/072* (2013.01); *A61B 17/07207* (2013.01); *A61B 34/30* (2016.02); *A61B 2017/07278* (2013.01)

(58) Field of Classification Search
CPC ............ A61B 17/072; A61B 17/07207; A61B 2017/07278; A61B 34/30
See application file for complete search history.

(56) References Cited

U.S. PATENT DOCUMENTS

| | | | | |
|---|---|---|---|---|
| 5,071,052 | A | * | 12/1991 | Rodak ................. A61B 17/072 227/124 |
| 5,307,976 | A | * | 5/1994 | Olson ............. A61B 17/07207 227/175.3 |
| 5,397,046 | A | * | 3/1995 | Savage ............ A61B 17/07207 227/175.3 |
| 5,415,335 | A | * | 5/1995 | Knodell, Jr. ...... A61B 17/07207 227/180.1 |
| 5,715,988 | A | * | 2/1998 | Palmer ............. A61B 17/07207 227/175.3 |
| 5,718,359 | A | * | 2/1998 | Palmer ............. A61B 17/07207 227/175.2 |

(Continued)

FOREIGN PATENT DOCUMENTS

EP 2772206 A2 9/2014

OTHER PUBLICATIONS

International Search Report and Written Opinion for PCT/US2017/046470 dated Jan. 24, 2018 (18 pages).

(Continued)

*Primary Examiner* — Alexander M Valvis
*Assistant Examiner* — Eduardo R Ferrero
(74) *Attorney, Agent, or Firm* — Mintz Levin Cohn Ferris Glovsky and Popeo, P.C.

(57) ABSTRACT

A surgical stapler including an end effector having various embodiments of a lockout assembly is described. The lockout assembly can control the rotation of a drive member that extends through the end effector. A sled can be positioned along the drive member and caused to translate along the drive member upon rotation of the drive member. As such, the lockout assembly can prevent movement of the sled by controlling the ability of the drive member to rotate. The lockout assembly can assist with preventing inadvertent firing of the end effector, such as when there is no cartridge present or a spent cartridge (e.g., the cartridge does not have any staples).

6 Claims, 9 Drawing Sheets

(56) References Cited

U.S. PATENT DOCUMENTS

| | | | |
|---|---|---|---|
| 6,109,500 A * | 8/2000 | Alli | A61B 17/07207 227/175.2 |
| 8,114,345 B2 | 2/2012 | Dlugos, Jr. et al. | |
| 8,882,792 B2 | 11/2014 | Dietz et al. | |
| 8,915,842 B2 | 12/2014 | Weisenburgh, II et al. | |
| 8,931,682 B2 | 1/2015 | Timm et al. | |
| 8,945,098 B2 | 2/2015 | Seibold et al. | |
| 9,649,110 B2 * | 5/2017 | Parihar | A61B 17/1155 |
| 2004/0007608 A1 * | 1/2004 | Ehrenfels | A61B 17/07207 227/176.1 |
| 2004/0232195 A1 * | 11/2004 | Shelton, IV | A61B 17/07207 227/175.1 |
| 2004/0232199 A1 * | 11/2004 | Shelton, IV | A61B 17/07207 227/175.2 |
| 2005/0023324 A1 * | 2/2005 | Doll | A61B 17/07207 227/175.2 |
| 2005/0173490 A1 * | 8/2005 | Shelton, IV | A61B 17/07207 227/175.2 |
| 2007/0039997 A1 * | 2/2007 | Mather | A61B 17/072 227/176.1 |
| 2007/0102475 A1 * | 5/2007 | Ortiz | A61B 17/07207 227/175.2 |
| 2008/0081948 A1 | 4/2008 | Weisenburgh et al. | |
| 2010/0193569 A1 | 8/2010 | Yates | |
| 2011/0006101 A1 * | 1/2011 | Hall | A61B 90/30 227/175.2 |
| 2011/0118709 A1 | 5/2011 | Burbank | |
| 2011/0118778 A1 | 5/2011 | Burbank | |
| 2012/0089131 A1 * | 4/2012 | Zemlok | A61B 17/07207 606/1 |
| 2012/0138660 A1 | 6/2012 | Shelton | |
| 2013/0037597 A1 * | 2/2013 | Katre | A61B 17/072 227/176.1 |
| 2013/0098965 A1 * | 4/2013 | Kostrzewski | A61B 17/07207 227/175.2 |
| 2013/0193188 A1 * | 8/2013 | Shelton, IV | A61B 17/068 227/175.2 |
| 2013/0282052 A1 | 10/2013 | Aranyi et al. | |
| 2014/0005677 A1 | 1/2014 | Shelton | |
| 2014/0005718 A1 | 1/2014 | Shelton, IV et al. | |
| 2014/0021239 A1 * | 1/2014 | Kostrzewski | A61B 17/07207 227/175.3 |
| 2014/0110453 A1 * | 4/2014 | Wingardner | A61B 17/07207 227/175.2 |
| 2014/0239041 A1 * | 8/2014 | Zerkle | A61B 17/07207 227/176.1 |
| 2014/0263545 A1 * | 9/2014 | Williams | A61B 17/068 227/175.2 |
| 2014/0263569 A1 * | 9/2014 | Williams | A61B 17/07207 227/180.1 |
| 2015/0289873 A1 * | 10/2015 | Shelton, IV | A61B 17/07207 227/176.1 |
| 2015/0324317 A1 * | 11/2015 | Collins | A61B 90/90 710/106 |
| 2015/0351765 A1 * | 12/2015 | Valentine | A61B 90/90 227/176.1 |

OTHER PUBLICATIONS

Correlated Solutions, "Principle of Digital Image Correlation," 2013 (http://correlatedsolutions.com/digital-image-correlation/).

U.S. Appl. No. 15/131,963 entitled "Method for Operating a Surgical Instrument" filed Apr. 18, 2016.

U.S. Appl. No. 15/177,430 entitled "Surgical Instrument With User Adaptable Techniques" filed Jun. 9, 2016.

* cited by examiner

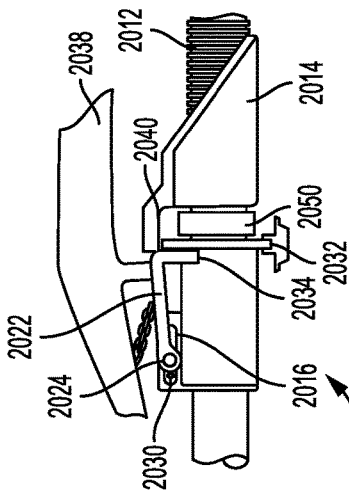
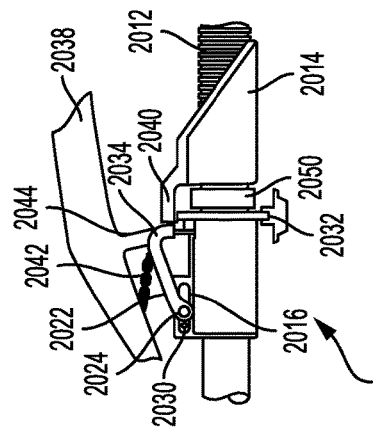
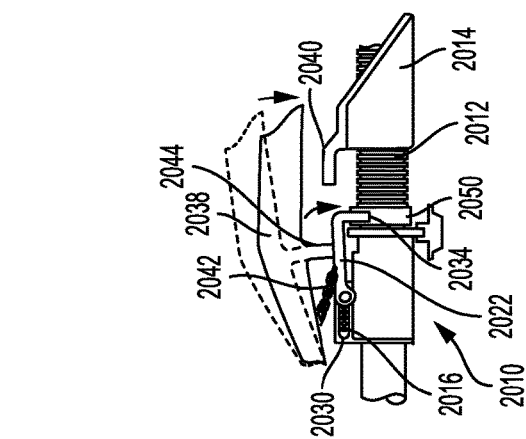
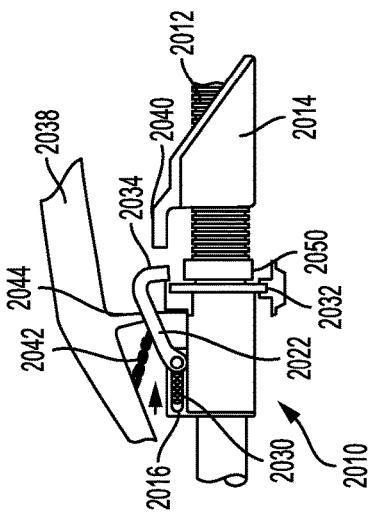
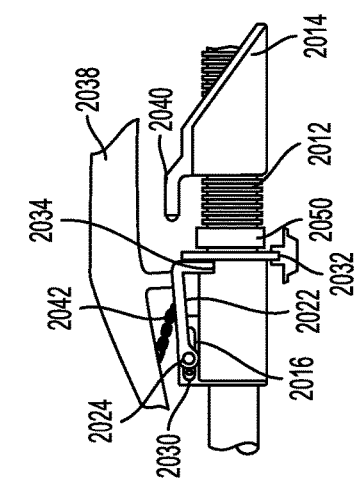

STAPLER TOOL WITH ROTARY DRIVE LOCKOUT

FIELD OF THE INVENTION

Surgical stapling methods and devices are provided, and in particular lockout devices and methods for locking a rotary drive element on a surgical stapler are provided.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Some end effectors utilize a rotary driver that extends at least part way through the end effector. The rotary driver can rotate to advance a sled along the rotary driver in a distal direction, thereby actuating the wedges to fire staples. Once firing is complete, it is undesirable to further advance the sled as this can cause the sled to project through the distal end of the end effector, damaging the device and potentially causing harm to the patient. In surgical staplers used in robotic systems, a sensor can be utilized to determine an end effector location or to determine whether firing has occurred. However, in the event of any electrical failure, it would be desirable to have a mechanical intervention to prevent further firing of a spent cartridge.

Accordingly, while significant advances have been made in the field of surgical staplers, there remains a need for a surgical stapler that prevents firing of a spent staple cartridge.

SUMMARY OF THE INVENTION

Surgical stapling devices and methods are provided for preventing firing of a surgical stapler when the jaws are in an open position and after the stapler has already been fired. In one embodiment, a surgical stapler includes a housing having an elongate shaft extending distally therefrom and an end effector coupled to a distal end of the elongate shaft. The end effector can include first and second jaws that are movable between an open position and a closed position, with the first jaw having a plurality of staples disposed therein. The surgical stapler can further include a rotary drive member extending through the elongate shaft and a sled coupled to the rotary drive member such that rotation of the rotary drive member is configured to advance the sled through the first jaw of the end effector to fire a plurality of staples into tissue engaged between the first and second jaws. In addition, the surgical stapler can include a lockout assembly that is linearly translatable between proximal and distal positions and that is pivotable about a pivot axis. The lockout assembly can be effective to prevent rotation of the rotary drive member after the sled is advanced distally through the first jaw.

In some variations one or more of the following features can optionally be included in any feasible combination. The lockout assembly can be pivotable between engaged and disengaged positions in each of the proximal and distal positions. The lockout assembly can be maintained in the proximal position when the sled is in a proximal-most position before being advanced through the first jaw, and the lockout assembly can move to the distal position after the sled is in a distal-most position after firing the plurality of staples and the jaws are moved to an open position. The lockout assembly can have various configurations, and in one embodiment can include a lockout body disposed around the rotary drive member and a latch pivotally and slidably coupled to the lockout body. The latch can be biased distally and can be configured to rotate about a pivot point when moving between the engaged and disengaged positions. The rotary drive member can include an engagement feature formed thereon that is configured to be engaged by the latch to prevent rotation of the rotary drive member. The engagement feature can include at least two flat sides that are configured to be engaged between at least two corresponding flat sides formed on the latch.

In other aspects, the sled can be configured to maintain the lockout assembly in the proximal position when the sled is in an initial proximal position, prior to being advanced through the first jaw. The sled can be configured to release the lockout assembly when the sled is advanced distally through the first jaw to allow the lockout assembly to move to the distal position. When the sled is in an initial position before being advanced through the first jaw, the second jaw can be configured to move the lockout assembly into the engaged position such that the lockout assembly is maintained in the proximal position. After the sled is advanced through the first jaw, the second jaw can be configured to release the lockout assembly to allow the lockout assembly to move from the proximal position to the distal position.

In another embodiment, the housing can be configured to couple to a plurality of motors on a tool driver of a surgical robotic system.

In another embodiment, a lockout mechanism is provided and includes a rotary drive member and an engagement feature disposed on the rotary drive member. The lockout mechanism can further include a lockout assembly having a lockout body disposed about the rotary drive member and a latch pivotally coupled to the lockout body about a pivot pin such that the latch pivots between engaged and disengaged positions. The latch and pivot pin can be configured to translate linearly along the lockout body between proximal and distal positions. The lockout assembly can further include a latch retainer positioned between the lockout body and the engagement feature on the rotary drive member. The latch can be configured to engage the latch retainer when the latch is in the proximal position and in the engaged position such that the latch retainer prevents movement of the latch to the distal position. The latch can be configured to engage the engagement feature on the rotary drive member when the latch is in the distal position and in the engaged position such that the latch prevents rotation of the rotary drive member.

In some embodiments, the latch includes a recess formed therein and has a shape complementary to the engagement feature for engaging the engagement feature to prevent rotation of the rotary drive member. The lockout assembly can further include a sled coupled to the drive member such that rotation of the drive member causes linear translation of the sled along the drive member. The sled can include a latch engager that maintains the latch in the proximal position when the sled is in a proximal-most position adjacent to the lockout assembly. The lockout assembly can further include a biasing element that biases the latch to the distal position.

In another aspect, a method for stapling tissue is provided and includes actuating a surgical stapler to rotate a rotary drive member that advances a sled through an end effector to fire a plurality of staples into tissue engaged between opposed jaws of the end effector. The end effector can include a lockout assembly that pivots from a disengaged position to an engaged position to prevent rotation of the rotary drive member after the sled is advanced through the end effector to fire the plurality of staples into the tissue engaged between the opposed jaws of the end effector. The lockout assembly can include a latch that pivots between the disengaged and engaged positions, and the latch can be configured to translate linearly along a main body of the lockout assembly. The sled can maintain the lockout assembly in a proximal position when the sled is in an initial position prior to being advanced through the end effector, and the sled can allow the lockout assembly to move to a distal position after the sled is advanced through the end effector. In some embodiments, actuating the surgical stapler can include providing an input to a surgical robot to activate a motor that causes rotation of the rotary drive member.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The invention will be more fully understood from the following detailed description taken in conjunction with the accompanying drawings, in which:

FIG. 9A illustrates the latch of the lockout assembly of FIG. 8, with the sled in a proximal position, the second jaw in an open position, and the latch rotated about a pivot point.

FIG. 9B illustrates a latch of the lockout assembly of FIG. 8, with the latch in a first position where the drive member is allowed to rotate.

FIG. 9C illustrates the sled of FIG. 9B in a distal position along the drive member relative to the lockout assembly.

FIG. 9D illustrates an engagement end of the latch of the lockout assembly of FIG. 8 moved from a proximal side to a distal side of a retainer.

FIG. 9E illustrates the latch of the lockout assembly of FIG. 8 being biased in the distal direction thereby positioning the engagement end of the latch on the distal side of the retainer and allowing the engagement end to engage with an engagement feature of the drive member thereby preventing the drive member from rotating and the sled from moving along the drive member.

DETAILED DESCRIPTION OF THE INVENTION

Figure 1:
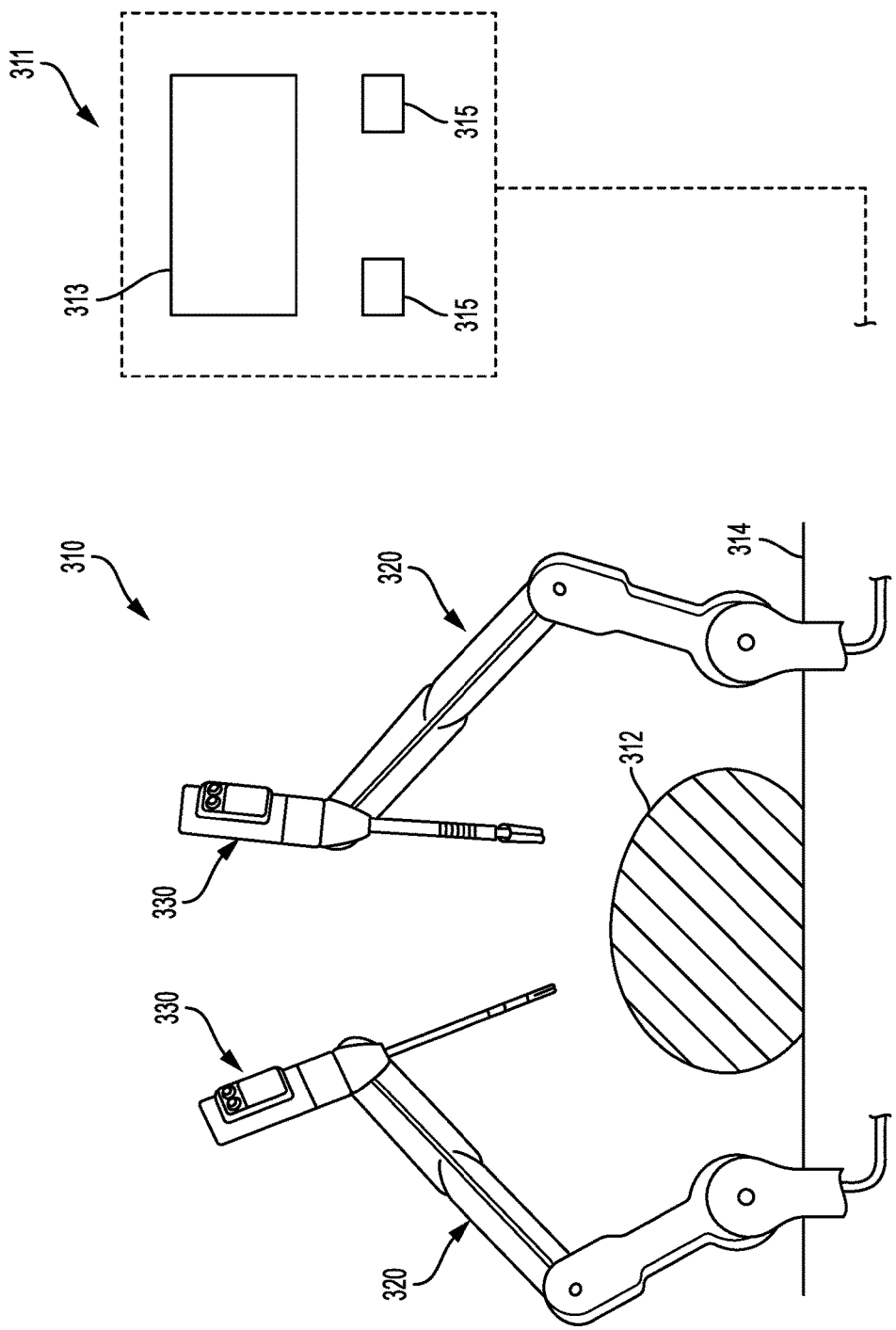
FIG. 1 illustrates a perspective view of one embodiment of a surgical robotic system a includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, a lockout is provided for preventing firing of a surgical stapler when the jaws are in an open position and after the stapler has already been fired. The lockout is advantageous in that it can be used to prevent rotation of a rotary firing assembly. In an exemplary embodiment, the lockout moves linearly between proximal and distal positions, and also pivots about an axis between engaged and disengaged positions to eventually prevent rotary motion of a drive screw that advances a sled assembly for firing staples from an end effector. While the lockout is disclosed herein in connection with a rotary firing assembly, the lockout is not limited to use with a firing assembly. The lockout can be used with any rotary drive assembly for driving any number of actuators, including rotary articulation rods, rotary closing assemblies, rotary rotation assemblies, etc. Moreover, while the lockout is disclosed herein in connection with a robotic tool used in a surgical robotic system, the lockout can be used in any surgical stapler device, including devices that are manually operated and devices that are powered.

As indicated above, in one embodiment the systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
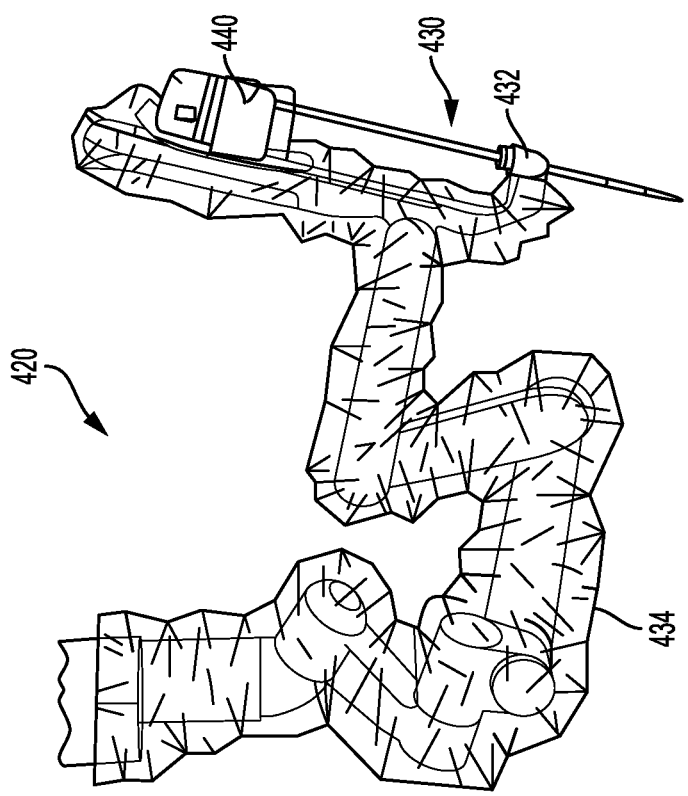
FIG. 2 illustrates an embodiment f a robotic arm a su robotic system with a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
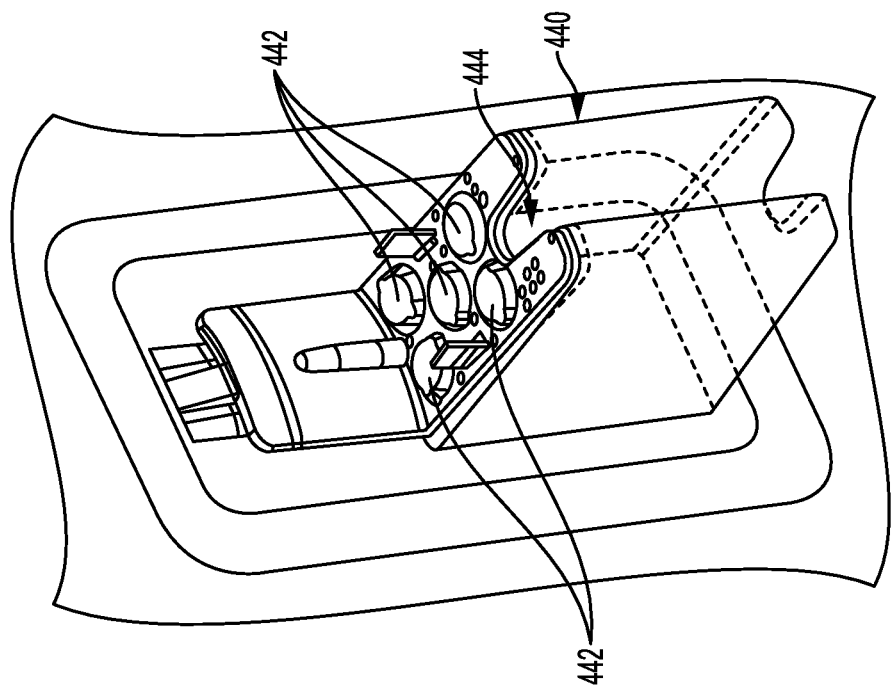
FIG. 3 illustrates a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
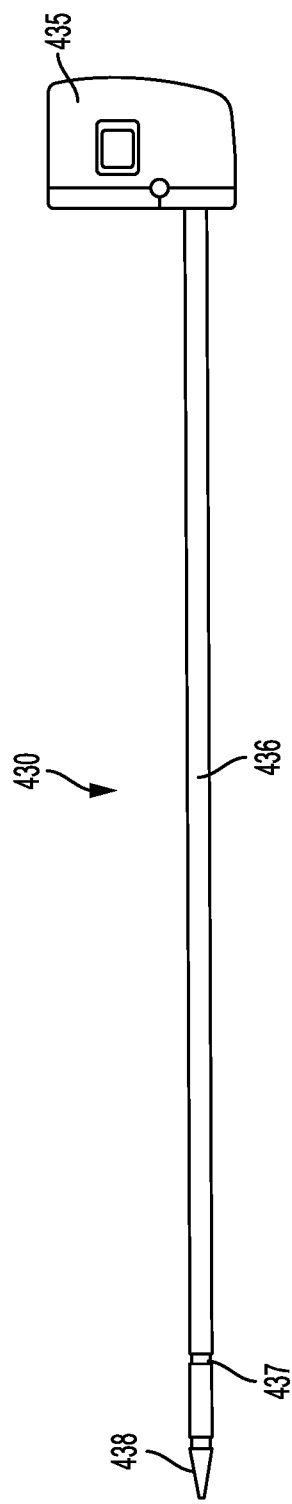
FIG. 4 illustrates the tool assembly of FIG. 2 uncoupled from the robotic arm, the tool assembly including a shaft extending from a puck at a proximal end and having an end effector located at a distal end of the shaft.

FIG. 4 illustrates the tool assembly 430 uncoupled from the robotic arm 420. The tool assembly 430 includes a housing or puck 435 coupled to a proximal end of a shaft 436 and an end effector 438 coupled to a distal end of the shaft 436. The end effector can include a pair of jaws, such as a second jaw that pivots relative to a first jaw. The second jaw can pivot between a closed position where the pair of jaws are configured to engage tissue therebetween and an open position where the pair of jaws are configured to receive tissue therebetween. A cartridge that holds staples can be disposed within the first jaw and one or more staples can be delivered to a surgical site upon firing of the end effector to staple tissue engaged therebetween. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
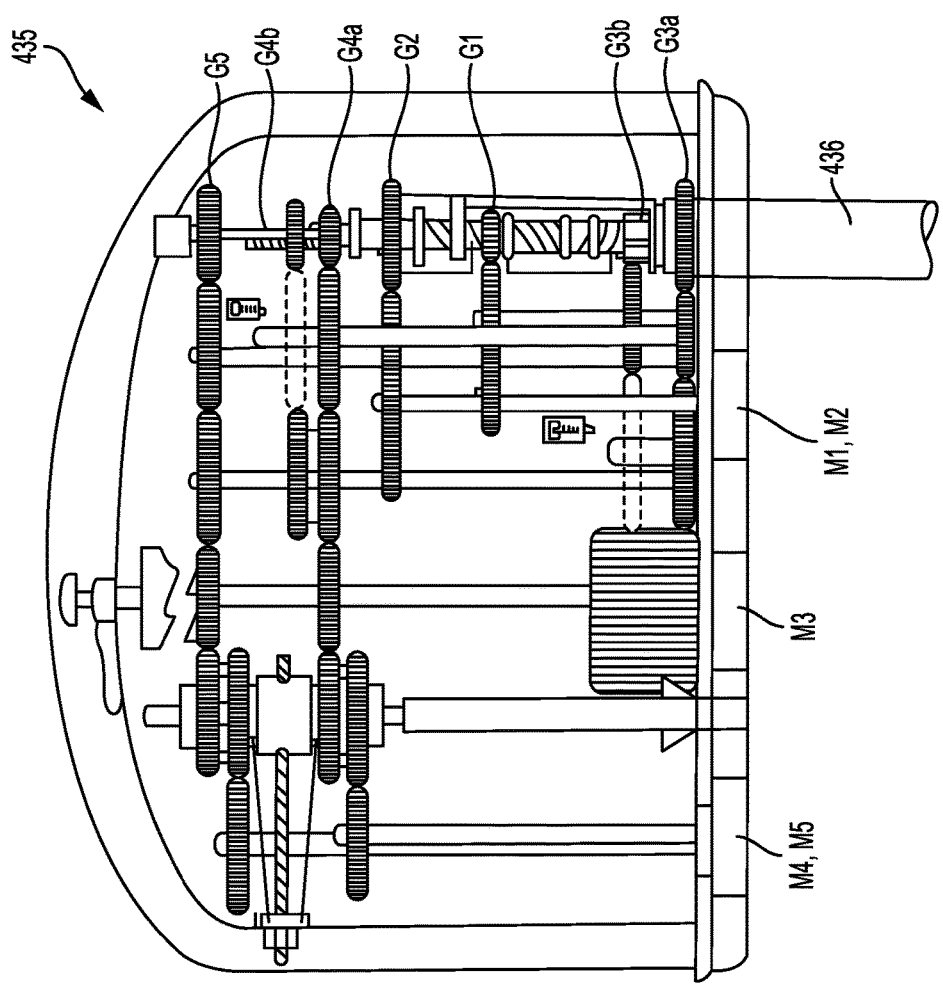
FIG. 5 illustrates the puck of the tool assembly of FIG. 4.

FIG. 5 illustrates the puck 435 and a proximal end of a shaft 436 extending from the puck 435 in more detail. As shown in FIG. 5, the puck 435 includes a plurality of actuation gears and gear shafts that can be either directly or indirectly controlled to any one of the motors 442 associated with the driver 440. For example, as shown in FIG. 5, the puck 435 is configured to couple to five motors at the locations indicated by reference numbers M1, M2, M3, M4, and M5. In this embodiment, puck 435 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The puck 435 also includes a shaft rotation gear G3a that is coupled to the third motor M3 via a series of one or more additional gears and shafts. Actuation of the third motor M3 will thus rotate the shaft rotation gear G3a thereby causing rotation of the shaft 436 of the tool assembly 430. The third motor M3 can also be configured to shift and to couple, via a series of one or more additional gears and shafts, to a head rotation gear G3b which will cause rotation of the end effector 438 relative to the shaft 436. The puck 435 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector 438. The puck 435 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 438. Finally, the illustrated puck 435 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438, as will be discussed in more detail below.

Figure 6:
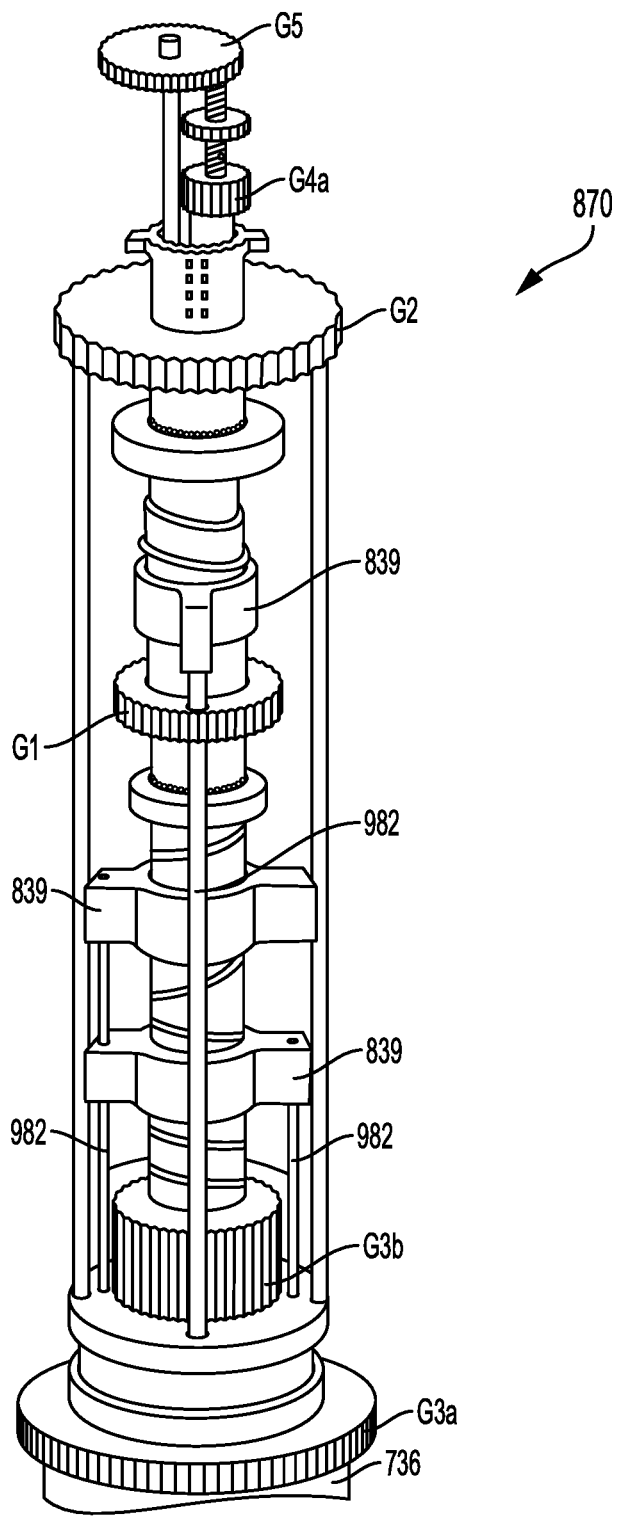
FIG. 6 illustrates an actuation assembly of the puck of FIG. 5.
Figure 7:
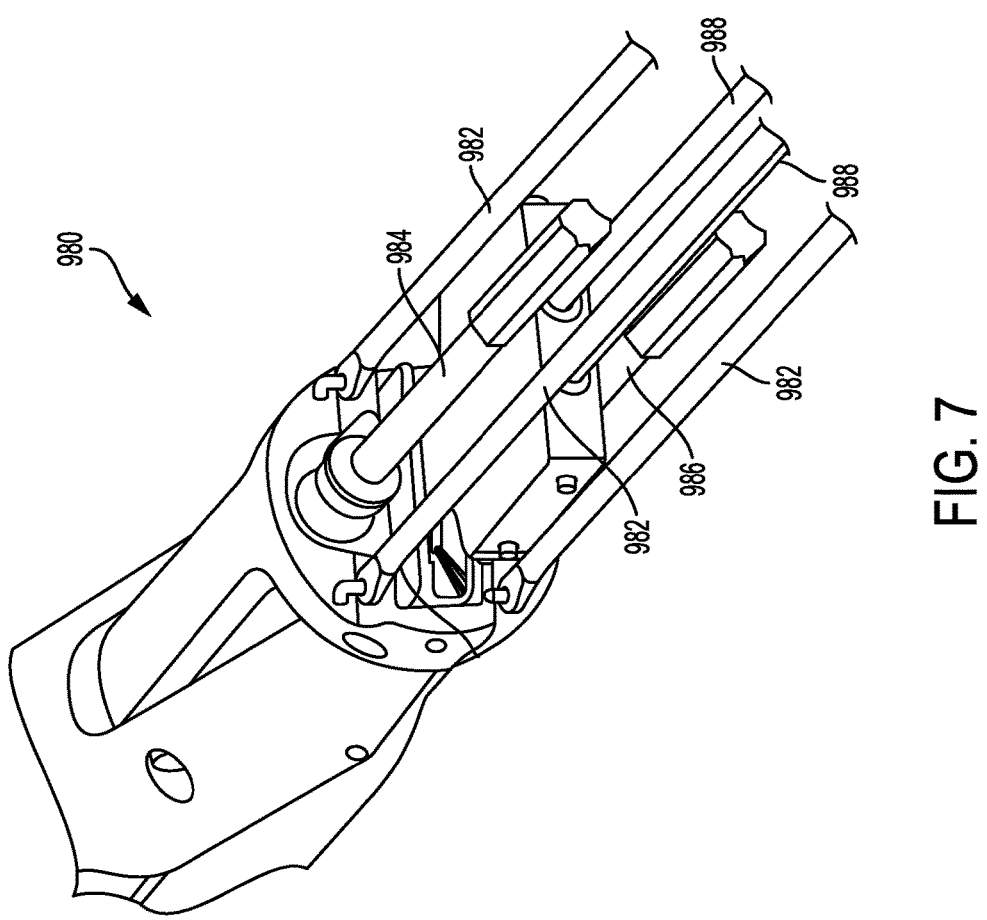
FIG. 7 illustrates actuation shafts extending from a wrist located just proximal of the end effector of FIG. 4.

FIG. 6 illustrates the actuation assembly 870 components of the puck 435 of FIG. 5. As shown and indicated above, each of the gears G1-G5 coupled to an actuation shaft that extends from the actuation assembly 870 and along the shaft 436 of the tool assembly 430, such as for controlling the movements of the end effector. FIG. 7 illustrates a distal end of the actuation shafts extending from a wrist 980 located just proximal of the end effector 438. The wrist 980 can allow for fine movements and angulation of the end effector 438 relative to the proximal end of the shaft 436. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector 438 (e.g., movement up, down, left, right, and combinations thereof) relative to the proximal end of the shaft 436. The articulation cables 982 are connected to the articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector 438 to firmly close. The upper rotary driver 984 is coupled to the firm close gear G4a shown in FIG. 6 such that rotation of the firm close gear G4a by the motor M4 causes rotation of the rotary driver 984. The wrist 980 can also include a lower rotary driver 986 that when actuated can cause movement of a sled located at the end effector 438. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4b shown in FIG. 6 and that moves linearly in a proximal direction to cause rapid close of the pair of jaws.

Figure 8:
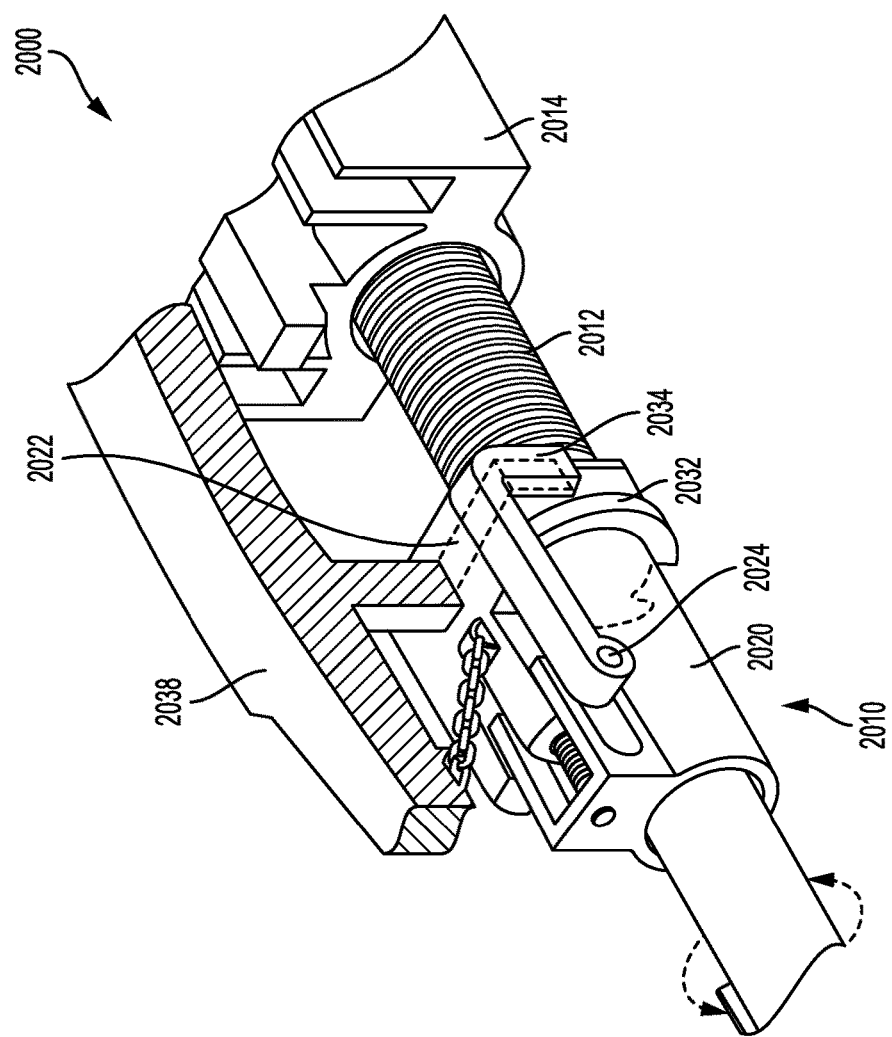
FIG. 8 illustrates an embodiment of a part of an end effector including a lockout assembly that controls the rotation of a drive member that extends through the end effector and the movement of a sled positioned along the drive member.

FIG. 8 shows an embodiment of a part of an end effector 2000 including a lockout assembly 2010 that selectively prevents rotation of a drive member 2012 that extends through the end effector 2000. A sled 2014 is positioned along the drive member 2012 such that rotation of the drive member 2012 causes linear translation of the sled 2014. The lockout assembly 2010 is effective to selectively prevent movement of the sled 2014 by selectively preventing rotation of the drive member 2012. The lockout assembly 2010 can prevent inadvertent firing, such as when the jaws are not closed and/or when there is no cartridge present or a spent cartridge (e.g., the cartridge does not have any staples).

As shown in FIG. 8, the lockout assembly 2010 includes a lockout body 2020 that is operatively coupled to the drive member 2012. The lockout body 2020 can include a key feature that prevents the lockout body 2020 from rotating with or relative to the drive member 2012. For example, an embodiment of the key feature can include an extension from the lockout body 2020 that mates with at least one of the jaws of the end effector 2000 thereby preventing the lockout body 2020 from rotating relative to the jaws. The key feature can mate with a feature associated with the jaws along where the lead screw resides (e.g., a channel that extends through the end effector). Some embodiments of the key feature can include welding a part of either the key feature or part of the lockout body 2020 to a part of the end effector that does not rotate when the drive member 2012 is rotated, such as the jaws. The key feature can have any number of configurations, including any number of shapes that mate with complimenting shapes associated with one or more parts of the end effector 2000, that allow for preventing the lockout body 2020 from rotating relative to the drive member 2012, all of which are within the scope of this disclosure. As such, when the drive member 2012 is rotated relative to the end effector, the lockout body 2020 remains non-rotatably fixed and does not rotate relative to the end effector 2000. The lockout body 2020 includes a latch 2022 that rotates about a pivot pin 2024 defining a pivot axis. The pivot pin 2024 can translate along a slot 2026 that extends a longitudinal distance along the lockout body 2020 in a direction that is parallel to the longitudinal axis of the lockout body 2020. Linear translation of the pivot pin 2024 along the slot 2026 allows the latch 2022 to move between proximal and distal positions. When the latch 2022 is in the proximal position, rotation of the latch 2022 about the pivot pin 2024 allows the latch 2022 to move between a proximal disengaged position (jaws open) and proximal engaged position (jaws closed). In both the proximal disengaged position and the proximal engaged position the drive member 2012 is free to rotate. When the latch 2022 is in the distal position, rotation of the latch 2022 about the pivot pin 2024 allows the latch 2022 to move between a distal disengaged position (jaws open) and a distal engaged position (jaws closed). In the distal engaged position (jaws closed), the latch prevents rotation of the drive member 2012.

The latch 2020 can have a variety of shapes and configurations, however, as shown in FIG. 8, the latch 2020 has an elongated L-shaped body with a first proximal end that includes a bore formed therethrough for receiving the pivot pin 2024, and a second distal or engagement end 2034 that extends substantially perpendicular to the longitudinal axis of the drive member 2012 when the latch is in the distal engaged position. The second distal or engagement end 2034 can be configured to engage a portion of the lockout body 2020 when in the proximal position, and it can be configured to engage the drive member 2012 or a driver engagement feature 2050 coupled to the drive member 2012 in the distal position.

A number of features in the end effector 2000 and/or part of the lockout assembly 2010 can assist with maintaining the latch 2022 in the first proximal position. For example, as shown in FIG. 8, a retainer 2032 can be formed on or positioned adjacent to a distal end of the lockout body 2020. The retainer 2032 can have a circumference that is greater than the lockout body 2020 such that the engagement end 2034 of the latch 2022 can abut against a proximal side of the retainer 2032 when the latch 2022 is in the proximal engaged position. The second jaw 2038 can assist with movement the latch 2022 between the proximal engaged position and the proximal disengaged position, as will be described in greater detail below.

FIG. 9A shows the latch 2022 in the proximal disengaged position, with the latch 2022 rotated about the pivot pin 2024 such that the latch 2022 is disengaged from the retainer 2032 on the latch body 2020 and the pivot pin 2024 is still located at the proximal end of the slot 2016. As shown in FIG. 9A, the sled 2014 is located adjacent a distal end of the lockout body 2020 in a proximal position. For example, the sled 2014 is in this proximal positon prior to firing (e.g., delivering a staple to a surgical site). The sled 2014 includes a first latch engager 2040 that extends proximally towards the latch 2022. When the sled 2014 is in the proximal position, the first latch engager 2040 extends a length such that it can abut against the engaging end 2034 of the latch 2022 when the engaging end 2034 is positioned above the outer edge of the retainer 2032 thereby preventing the latch 2022 from advancing in the distal direction.

FIG. 9B shows the latch 2022 in the proximal engaged position where the latch 2022 is engaged with the retainer 2032 on the latch body 2020 and the pivot pin 2024 is located at a proximal end of the slot 2026. The latch 2022 is biased in the distal direction as a result of a latch spring 2030 acting on the pivot point 2024 and forcing the latch 2022 towards a distal end of the slot 2016. However, as shown in FIG. 9B, the latch 2022 can be prevented from moving in the distal direction due to at least one force acting against the latch spring 2030. More specifically, the retainer 2032 positioned adjacent a distal end of the lockout body 2020 includes an outer diameter that is greater than the latch body 2020 thereby providing a proximal surface that the engagement end 2034 of the latch 2022 can abut against when in the first position (as shown in FIG. 9B). The latch 2022 can also be prevented from pivoting along the pivot 2020 as a result of the second jaw 2038 applying a force against the latch 2022 thereby forcing the latch against the latch body 2020.

The second jaw 2038 can include a second latch engager 2044 that extends from a bottom side of the second jaw 2038 towards the latch 2022. The second latch engager 2044 can apply a force against a top side of the latch 2022 when the second jaw 2038 moves from an open position to a closed position to force the latch 2022 to rotate from the proximal disengaged position, towards the lockout body 2020, to the proximal engaged position. As such, when the latch 2022 is in the proximal engaged position, the second latch engager 2044 forces the latch 2022 to engage the retainer 2032 on the lockout body 2020, as shown in FIG. 9B.

The second jaw 2038 can also include a latch connector 2042 that extends between and is coupled to the second jaw 2038 and the latch 2022. The latch connector 2042 can have a length that causes the latch 2022 to rotate about the pivot pin 2024 from the proximal engaged position to the proximal disengaged position when the second jaw 2038 is moved from the closed position to the open position. For example, as shown in FIG. 9A, when the second jaw 2038 is moved to the open position, the latch connector 2042 pulls the latch 2022 to cause it to rotate about the pivot pin 2024 and disengage from the retainer 2032 on the lockout body 2020. The latch connector 2042 can be made out of one or more of a spring, an elastic member, and an inelastic member. In other embodiments, a biasing element can be used to bias the latch 2022 to the disengaged position.

FIG. 9C shows the sled 2014 in a distal position, such as after rotating the drive member 2012 and firing of the cartridge. When the jaws are closed and the sled 2014 is translated through the end effector to a distal position, the retainer 2032 will prevent the latch 2022 from advancing in the distal direction. The latch 2022 is thus maintained in the proximal engaged position. However, after firing, when the second jaw 2038 moves into the open position, the latch connector 2042 pulls the latch 2022 such that the latch 2022 rotates about the pivot pin 2024 into the proximal disengaged position. In this position, the engagement end 2034 lifts up and moves away from the retainer 2032. Thus, neither the retainer 2032 nor the first latch engager 2040 on the sled 2014 prevents the latch from moving in a distal direction. As such, the latch spring 2030 forces the latch 2022 and the pivot pin 2024 in the distal direction along the slot 2016 thereby moving the engagement end 2034 of the latch 2022 to a position distal of the retainer 2032, as shown in FIG. 9D. The latch 2022 is thus moved to the distal disengaged position. The latch spring 2030 biases the latch 2020 such that the engagement end 2034 of the latch 2022 is maintained in the distal position on the distal side of the retainer 2032 and a latch engagement feature 2048 (FIG. 10) located at the engagement end 2034 of the latch 2022 is aligned with a driver engagement feature 2050 on the drive member 2012, as discussed in more detail below.

FIG. 9E shows the second jaw 2038 moving into the closed position, after firing and opening the second jaw 2038, thereby forcing the latch 2022 into the distal engaged position. The second latch engager 2044 of the second jaw 2038 can apply a force to the latch 2022 to cause the latch 2022 to rotate about the pivot pin 2024 and move toward the drive member 2012 into the distal engaged position. In this position, the latch engagement feature 2048 engages the driver engagement feature 2050 thereby preventing the drive member 2012 from rotating.

The driver engagement feature 2050 is located adjacent the distal side of the retainer 2032 and is complementary in shape to the latch engagement feature 2048. The driver engagement feature 2050 is configured such that it does not rotate independent of the drive member 2012. As such, when the latch engagement feature 2048 is in engagement with the driver engagement feature 2050 to prevent rotation thereof, the drive member 2012 is also prevented from rotating.

Figure 10:
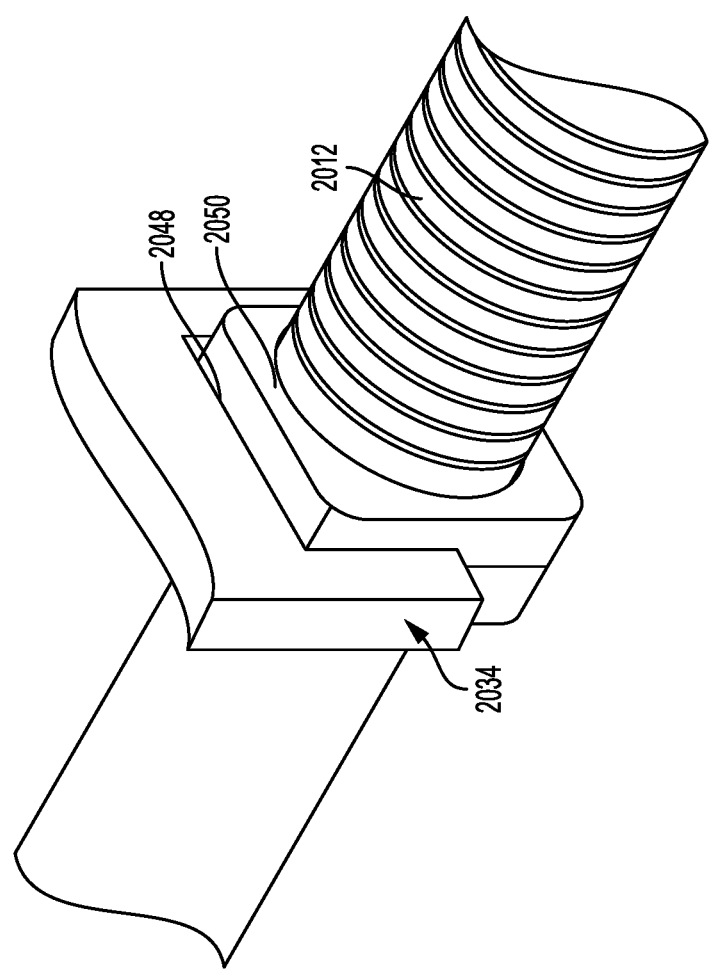
FIG. 10 illustrates a latch engagement feature of the latch of FIG. 8 coupled to a driver engagement feature of the drive member.

FIG. 10 shows one embodiment of the latch engagement feature 2048 coupled to the driver engagement feature 2050. As shown, the latch engagement feature 2048 is in the form of a square recess formed in the latch 2034, and the driver engagement feature 2050 has a complementary square shape so as to be matingly received within the recess. For example, the first and second square features can include at least two flat sides angled relative to each other, such as approximately a ninety degree angle. When engaged, the first and second square features prevent rotation of the driver engagement feature 2050 relative to the latch engagement feature 2048. The driver engagement feature 2050 cannot rotate independently from the drive member 2012, thus when the driver engagement feature 2050 is prevented from rotating, the drive member 2012 is also prevented from rotating. This also prevents the sled 2014 from translating, thereby preventing further firing of the end effector.

Although the latch engagement feature 2048 and driver engagement feature 2050 are shown as having a square shape including at least two flat sides, the latch engagement feature 2048 and driver engagement feature 2050 can have a variety of shapes that allow the latch engagement feature 2048 and driver engagement feature 2050 to become engaged thereby preventing the driver engagement feature 2050 from rotating relative to the latch engagement feature 2048.

There are several general aspects that apply to the various descriptions herein. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A lockout mechanism for use with a surgical stapler, comprising:
   a rotary drive member;
   an engagement feature disposed on the rotary drive member; and
   a lockout assembly having
      a lockout body disposed about the rotary drive member,
      a latch pivotally coupled to the lockout body about a pivot pin such that the latch pivots between engaged and disengaged positions, the latch and pivot pin being configured to translate linearly along the lockout body between proximal and distal positions, and
      a latch retainer positioned between the lockout body and the engagement feature on the rotary drive member;
   wherein the latch is configured to engage the latch retainer when the latch is in the proximal position and in the engaged position such that the latch retainer prevents movement of the latch to the distal position; and
   wherein the latch is configured to engage the engagement feature on the rotary drive member when the latch is in the distal position and in the engaged position such that the latch prevents rotation of the rotary drive member.

2. The lockout mechanism of claim 1, wherein the latch includes a recess formed therein and having a shape complementary to the engagement feature for engaging the engagement feature to prevent rotation of the rotary drive member.

3. The lockout mechanism of claim 1, further comprising a sled coupled to the drive member such that rotation of the drive member causes linear translation of the sled along the drive member.

4. The lockout mechanism of claim 3, wherein the sled includes a latch engager that maintains the latch in the proximal position when the sled is in a proximal-most position adjacent to the lockout assembly.

5. The lockout mechanism of claim 3, wherein the sled is configured to release the lockout assembly when the sled is advanced distally to allow the lockout assembly to move to the distal position.

6. The lockout mechanism of claim 1, further comprising a biasing element that biases the latch to the distal position.

* * * * *